United States Patent [19]

Ozbalik

[11] Patent Number: 5,250,737
[45] Date of Patent: Oct. 5, 1993

[54] PROCESS FOR HYDROCARBYL TRISULFIDE PRODUCT

[75] Inventor: Nubar Ozbalik, Baton Rouge, La.

[73] Assignee: Ethyl Corporation, Richmond, Va.

[21] Appl. No.: 828,561

[22] Filed: Jan. 31, 1992

[51] Int. Cl.$^5$ .......................................... C07C 319/24
[52] U.S. Cl. .......................................... 568/21; 568/26
[58] Field of Search .......................................... 568/21, 26

[56] References Cited

U.S. PATENT DOCUMENTS

| | | | |
|---|---|---|---|
| 2,237,625 | 4/1941 | Olin | 260/125 |
| 2,558,221 | 6/1951 | Mertz et al. | 260/608 |
| 2,574,884 | 11/1951 | Mertz et al. | 260/608 |
| 3,022,351 | 2/1962 | Mihan et al. | 260/608 |
| 3,275,693 | 9/1966 | Bapseres et al. | 260/608 |
| 3,308,166 | 3/1967 | Biensan et al. | 260/608 |
| 3,314,999 | 4/1967 | Bapseres et al. | 260/608 |
| 3,340,324 | 9/1967 | Warner | 260/608 |
| 3,392,201 | 7/1968 | Warner | 260/608 |
| 3,452,100 | 6/1969 | Bennett et al. | 260/608 |
| 3,510,426 | 5/1970 | Papay | 252/46.6 |
| 3,583,915 | 6/1971 | Myers | 252/46.6 |
| 3,703,504 | 11/1972 | Horodysky | 260/139 |
| 3,703,505 | 11/1972 | Horodysky et al. | 260/139 |
| 3,755,461 | 8/1973 | Kvasnikoff et al. | 260/608 |
| 3,994,979 | 11/1976 | Warner | 260/608 |
| 4,277,623 | 7/1981 | Kubicek | 568/26 |
| 4,288,627 | 9/1981 | Kubicek | 568/26 |
| 4,564,709 | 1/1986 | Koyama et al. | 568/26 |
| 4,744,912 | 5/1988 | Cardis | 252/46.7 |
| 4,900,460 | 2/1990 | Cardis | 252/46.6 |
| 4,933,481 | 6/1990 | Vallee et al. | 568/26 |
| 4,937,385 | 6/1990 | Buchholz et al. | 568/26 |
| 5,068,445 | 11/1991 | Arretz | 568/21 |

FOREIGN PATENT DOCUMENTS

| | | | |
|---|---|---|---|
| 839767 | 4/1970 | Canada | 260/609.5 |
| 885990 | 11/1971 | Canada | 260/609.5 |
| 0025944 | 9/1980 | European Pat. Off. | 149/12 |
| 10559 | 2/1982 | Japan | 149/12 |
| 140063 | 2/1982 | Japan | 149/12 |
| 1160473 | 6/1967 | United Kingdom | 149/12 |

*Primary Examiner*—Marianne M. Cintins
*Assistant Examiner*—Margaret J. Page
*Attorney, Agent, or Firm*—David E. LaRose

[57] ABSTRACT

A method for preparing an essentially chlorine free additive mixture for oleaginous fluids containing less than 15 wt. % dialkyl higher-polysulfides, the process comprising: a) forming a reaction mass comprising olefin, a sulfur source, and a catalyst; b) heating the reaction mass to a temperature and for a period of time which is sufficient to form a mixture of olefin, alkyl mercaptan, dialkyl disulfide, dialkyl trisulfide and dialkyl higher-polysulfides; and c) refluxing the reaction mass obtained in (b) at a temperature and for a period of time which are sufficient to convert at least a portion of the dialkyl higher-polysulfides to dialkyl trisulfide so as to obtain the additive mixture containing less than 15 wt. % dialkyl higher-polysulfides.

19 Claims, No Drawings

PROCESS FOR HYDROCARBYL TRISULFIDE PRODUCT

BACKGROUND

This invention relates to a process for production of dihydrocarbyl polysulfides, and more particularly to a process for selective synthesis of dihydrocarbyl trisulfide.

Methods for preparing dihydrocarbyl polysulfides, such as dialkyl polysulfides based on the use of mercaptans and sulfur as raw materials are well known in the art and are described for example in U.S. Pat. Nos. 2,237,625, 3,022,351, 3,275,693, 3,308,166, 3,314,999, 3,340,324, 3,392,201, 3,452,100, 3,755,461, 3,994,979, 4,564,709, 4,876,389, 4,933,481, and 4,937,385; British Pat. Spec. No. 1,160,473; Canadian Pat. Nos 839,767 and 885,990; European Pat. App. Pub. Nos. 25,944 and 337,837; and Japan Kokai (Laid-Open application) Nos. 58-140,063 and 59-10559.

Another approach for producing dihydrocarbyl polysulfides involves oxidizing a mercaptan with air or free oxygen in the presence of a catalyst. In U. S. Pat. No. 2,558,221 the catalyst is a selected natural bauxite which contains on a weight basis 50-70% $Al_2O_3$, 8-20% $Fe_2O_3$, 2-8% $SiO_2$, 0.5-5% $TiO_2$, and 2-30% volatile matter as determined by ignition at 1800° F. In U.S. Pat. No. 2,574,884 the catalyst is alumina associated with a minor amount of vanadia, magnetic iron oxide or chromia. In U.S. Pat. No. 4,277,623 a catalyst system comprising a cobalt molybdate-alkali metal and-/or alkaline earth metal hydroxide is used as the oxidation catalyst. And in U.S. Pat. No. 4,288,627 the oxidation catalyst is a supported cobalt molybdate catalyst used in combination with a liquid tertiary amine.

It is also known that dihydrocarbyl polysulfides can be formed by reacting mercaptans with sulfur chlorides such as sulfur monochloride and sulfur dichloride.

Buchholz, et al. describe a continuous process for preparing dialkyl disulfides by reacting an alkyl alcohol and hydrogen sulfide in one reaction zone over a solid particulate catalyst, and then passing the reactor effluent into a second reaction zone where it is reacted as a vapor with elemental sulfur in the presence of the same or a different solid, particulate catalyst.

Of the various dihydrocarbyl polysulfides, dihydrocarbyl trisulfides are particularly desirable for use as antiwear and extreme pressure lubricant additives because of their superior performance capabilities and their generally lower corrosiveness towards "yellow metals" such as copper. Dihydrocarbyl higher-polysulfides (e.g. polysulfides with more than about 3 sulfur atoms per molecule) are less desirable than polysulfides containing 3 or less sulfur atoms per molecule. Hence, one object of this invention is to provide a process which yields additives containing a high percentage of dihydrocarbyl di- and tri-sulfides and less dihydrocarbyl higher-polysulfides.

Another object of this invention is to provide a process for producing dihydrocarbyl polysulfides of the formula, R—$S_x$—R, where R is hydrocarbyl and x is an integer representing the average number of sulfur atoms in the product and is above 2.0, e.g., at least 2.5, and preferably is in the range of about 2.7 to 3.5.

The Invention

This invention involves, inter alia, the discovery that it is possible to prepare an essentially chlorine free additive mixture for oleaginous fluids containing less than 15 wt. % dialkyl higher-polysulfides. The process comprises: (a) forming a reaction mass comprising olefin, a sulfur source, and a catalyst; (b) heating the reaction mass to a temperature and for a period of time which is sufficient to form a reaction mixture of olefin, alkyl mercaptan, dialkyl disulfide, dialkyl tri-sulfide and dialkyl higher-polysulfides; and (c) refluxing the reaction mixture obtained in (b) at a temperature and for a period of time which are sufficient to convert at least a portion of the dialkyl higher-polysulfides to dialkyl trisulfide thereby obtaining the additive mixture containing less than 15 wt. % dialkyl higher polysulfides.

This invention provides an economical process for selectively preparing mixtures containing a predominant amount of dihydrocarbyl trisulfide from isobutylene, sulfur, and hydrogen sulfide. Such mixtures are useful as anti-wear and/or extreme pressure agents in oleaginous fluids. In general, this invention enables high yield synthesis of dihydrocarbyl trisulfide mixtures containing less than 15 wt. % hydrocarbyl higher-polysulfides having more than about 3 sulfur atoms per molecule. Such hydrocarbyl higher-polysulfides have been found to be less desirable to use in oleaginous formulations due to increased corrosion potential. Hydrocarbyl polysulfides wherein the average number of sulfur atoms in the product is in the range of about 2 to about 3 can also be formed by the process of this invention. Products of this type are also of known utility in the chemical and allied arts.

In one of its preferred forms, this invention provides a process enabling selective conversion of dialkyl higher-polysulfides to dialkyl trisulfide in high yields.

A particularly key feature of the process of this invention is the substantial absence of halogens in the reactants and products thus formed. Hence, the products of this invention exhibit low copper corrosivity which is desirable from the standpoint of an extreme pressure, anti-wear lubricant additive. Other features of the invention will be evident from the ensuing description and appended claims.

In another embodiment, this invention provides a process for preparing an essentially chorine free mixture containing more than about 40 wt. % dialkyl trisulfide and having less than 15 wt. % dialkyl higher-polysulfides. The process comprises, first reacting (i) olefin, (ii) hydrogen sulfide, (iii) flowers of sulfur, and (iv) a catalytic amount of an alumina catalyst at a temperature and for a period of time sufficient to form a reaction mixture containing olefin, alkyl mercaptan, and dialkyl polysulfides. Once formed this reaction mixture is then refluxed for a period of time sufficient to form the mixture comprising more than about 40 wt. % dialkyl trisulfide, and less than 15 wt. % dialkyl higher-polysulfides.

Olefins suitable for the process of this invention are the monoethylenically unsaturated aliphatic hydrocarbons referred to as aliphatic monoolefins containing 3 to about 12 carbon atoms. These include propylene, 1-butene, 2-butene, isobutene, 1-pentene, 2-pentene, 2-methyl-1-butene 3-methyl-1-butene, 2-methyl-2-butene, 1-hexene, 2-hexene, 3-hexene, 2-methyl-1-pentene, 2-methyl-2-pentene, 2-ethyl-2-butene and the like including mixtures and oligomers thereof. The olefins useful in the process of this invention are not critical. Hence, higher olefins may also be used provided they are suitably reactive under the process conditions set forth herein.

Preferably, the olefins are branched chain olefins such as isobutylene, 2-methyl-i-butene, 1-methyl-2-butene, 2-methyl-2-pentene and the like. More preferably, the ethylenical double bond adjoins a tertiary carbon atom such as isobutylene, the most preferred olefin.

Sulfur sources useful in the process of this invention include elemental sulfur in the form of precipitated sulfur or flowers of sulfur, alkali metal and alkaline-earth metal sulfides, hydrogen sulfide, and the like, or mixtures thereof. Use can be made, however, of any form or source of sulfur that is coreactive with the olefin being used. While many different sources of sulfur may be used, it is less desirable to utilize sulfur compounds containing halides, as the sulfurized olefin products thus obtained may have to be further purified to reduce the halogen content of the product to a low level. Although powdered forms of sulfur are generally employed, it is possible to use molten sulfur. Particularly preferred sulfur sources include hydrogen sulfide or flowers of sulfur and most preferred is a combination of hydrogen sulfide and flowers of sulfur as the sulfur source.

The relative proportions of sulfur and hydrogen sulfide can be varied within relatively wide limits (e.g., from about 1:5 to about 1:0.5 gram atoms of sulfur per mol of hydrogen sulfide to produce a wide variety of dihydrocarbyl polysulfides. When it is desired to form dihydrocarbyl trisulfide with high selectivity, a ratio of about 1:2 to about 1:1 gram atoms of sulfur per mol of hydrogen sulfide should be used.

The mole ratio of olefin to gram atoms of sulfur in the reaction mass is another key feature of this invention. In general, the higher the ratio of sulfur to olefin, the higher the sulfur content of the dihydrocarbyl polysulfide product. Typically, the mole ratio of olefin to gram atoms of sulfur is greater than about 1:1. When isobutylene is the olefin used, the mole ratio is more preferably, from about 1:0.1 to about 1:0.9 and most preferably, from about 1:0.5 to about 1:0.8.

To form the reaction mixture containing olefin, alkyl mercaptan, dialkyl disulfide, dialkyl trisulfide and dialkyl higher-polysulfides, a reaction temperature is selected which is sufficient to form the mixture from olefin and a sulfur source in the presence of catalyst. A useful reaction temperature ranges from about 50° C. to about 200° C., preferably, from about 70° C. about 150° C., and most preferably, from about 110° C. to about 120° C.

At the above preferred reaction temperature, the reaction will typically be conducted at superatmospheric pressures, especially when isobutylene is the olefin source and hydrogen sulfide is used as a sulfur source. Although the pressure is not critical to the process of the invention, a suitable pressure should be selected so that some or substantially all of the reactants remain in the liquid phase. Typically the reaction pressure will range from about 2 atmospheres to about 65 atmospheres or higher.

Suitable catalysts may be acidic, basic or neutral. Useful neutral and acidic materials include acidified clays, p-toluenesulfonic acid, diakylphosphorodithioic acids, phosphorus sulfides, such as phosphorus pentasulfide, and alumina catalysts. Basic catalysts include inorganic oxides and salts such as sodium hydroxide, calcium oxide, magnesium oxide, and sodium sulfide. Preferred catalysts are the alumina containing catalysts such as silica-alumina and aluminum oxide materials with aluminum oxide being the most highly preferred catalyst material.

Although an alumina containing catalyst is preferred, it is not known what catalyst transformations, if any, take place in situ during the reaction, and thus the identity of the actual catalytic species responsible for the reaction enhancement brought about by use of alumina is not known. The alumina catalyst typically remains active for an extended period of time; however, with repeated use, a portion of the catalyst may be deactivated during the reaction. Whatever its form and/or composition, this invention involves the use of any suitably active alumina catalyst in the process.

In a particularly preferred embodiment, the alumina catalyst is an activated alumina catalyst. The alumina catalyst may be activated by heating to an elevated temperature above 200° C. in a pressure vessel under an inert gas atmosphere, e.g. nitrogen, argon, helium, and the like. Such activated alumina catalysts typically have an average particle size in the range of from about 80 to about 200 mesh.

In another embodiment, the alumina catalyst is recycled from one run to the next. This procedure can be repeated, while augmenting the catalyst with fresh catalyst if necessary or desired, so long as the catalyst remains catalytically active in the process. When conducting the process with the objective in mind of forming dihydrocarbyl trisulfide with high selectivity, it is desirable to employ fresh catalyst or recycled catalyst which has not lost its ability to provide a product enriched in the trisulfide product. The number of times a given quantity of catalyst can be reused will depend on the characteristics of the particular catalyst selected for use and the particular reaction conditions under which it is used, but can be readily determined by the simple expedient of performing a few trial experiments in which the selected catalyst is recycled in a series of runs conducted under a selected set of reaction conditions.

The amount of catalytic material initially charged to the reaction vessel as aluminum oxide is generally in the range of from about 0.005 to about 0.1 moles per mole of olefinic compound charged. Preferably, the catalyst is charged such that the mole ratio of catalyst to olefin is in the range of from about 0.01:1 to about 0.06:1 moles of catalyst per mole of olefin, and most preferably, from about 0.03:1 to about 0.05:1 moles of catalyst per mole of olefin.

Reaction times generally fall in the range of about 0.5 to about 10 hours or more, and preferably are in the range of about 3 to about 4 hours. Those skilled in the art will recognize that the reaction time is dependant on size of the reaction equipment, and the volume of reactants utilized.

Subsequent to forming the reaction mixture, the reaction mixture is agitated or stirred for a period of time sufficient to essentially complete the reaction between the olefin and the sulfur source, and to dissolve a substantial amount of the formed alkyl mercaptan in the reaction mixture. The agitation period may range from 10 minutes to about 10 hours or more. Typically, the reaction is complete after about 3-4 hours depending on the amount of reactants present in the reaction mixture. It is critical to the invention that the reaction mass and reaction mixture be stirred or subjected to other forms of physical agitation in order to insure intimate contact among the reactants and catalyst in the reaction mixture.

The order of addition of reactants to the reaction mass is another key feature of the process of this invention. Preferably, solid sulfur and alumina catalyst are charged to the reaction vessel, and the reaction vessel is cooled to less than 10° C., preferably, less than 0° C., and most preferably to about −20° C. before charging the rest of the reactants. The order of addition of the sulfur and alumina catalyst to the reaction mass is, however, not critical to the invention. It is desirable, but not required to charge the hydrogen sulfide to the reaction vessel after charging the olefin to the reaction vessel in order to more easily control the reaction vessel pressure during reactant charging.

As the reaction proceeds, alkyl mercaptan is generally formed as a byproduct. The alkyl mercaptan is preferably retained in the reaction mixture subsequent to its formation by stirring the reaction mixture for a period of time, preferably about 3 hours or more, and then cooling the reaction mixture to a temperature of less than about 35° C., preferably in the range of from about 10° to about 20° C. Removal of hydrogen sulfide and unreacted olefin from the reaction mixture may be performed by methods well known by those skilled in the art. One method which may be used to remove unreacted olefin and hydrogen sulfide is to gradually reduce the reaction vessel pressure and then purge the vapor space above the reaction mixture with an inert gas such as nitrogen, argon, helium, or the like. Such unreacted olefin and hydrogen sulfide may then be collected and utilized in subsequent trisulfide reactions sequences. The means for removal of excess hydrogen sulfide and olefin is not critical to the invention.

Ordinarily, the reaction to form the reaction mixture can be conducted in the absence of a solvent. If it is desirable to use a solvent for forming the reaction mixture, the solvent should be one in which the reactants are mutually soluble, and which can be easily removed at the end of the reaction. The refluxing post-treating of the reaction mixture is preferably conducted in the substantial absence of solvent.

When the first reaction is complete, the reaction mixture is refluxed for a period of time sufficient to form the mixture comprising more than about 40 wt. % dialkyl trisulfide, and less than 15 wt. % dialkyl higher-polysulfides. Prior to refluxing, the reaction mixture is cooled, as indicated above, to dissolve alkyl mercaptan and unreacted olefin, and then purged for a period of time sufficient to remove a substantial portion of any remaining hydrogen sulfide and olefin. Once purged, the reaction mixture is heated to reflux to convert at least a portion of the dihydrocarbyl higherpolysulfides to dihydrocarbyl trisulfide. When the olefin is isobutylene, the reflux temperature will typically be in the range of from about 80° to about 120° C. and preferably from about 90° to about 110° C.

Reflux of the reaction mixture is maintained for a period of time which is sufficient to convert at least a portion of the dihydrocarbyl higher-polysulfides to di-hydrocarbyl trisulfide thereby forming the additive mixture containing more than about 40 wt. % dihydrocarbyl trisulfide, and less than 15 wt. % dihydrocarbyl higher-polysulfides. Reaction times will vary depending on the selected reaction temperature. In general, the reflux step proceeds rapidly. In most cases, the conversion of the dihydrocarbyl higher-polysulfides will be complete in less than 5 hours, preferably, less than 1 hour, but may take longer depending on the volume of the reaction mass and the ability to maintain a reaction temperature within the desired range. In a particularly preferred embodiment of the invention, the refluxed additive mixture contains less than about 6 wt. % dihydrocarbyl higher-polysulfides.

Reaction pressure for the reflux step is not critical to the invention. The pressure may thus range from subatmospheric to superatmospheric. It is desirable, however, to reflux the reaction mixture at substantially atmospheric pressure so that hydrogen sulfide that forms as a byproduct is easily removed from the reaction mixture during the reaction.

Reflux of the reaction mixture is preferably conducted while agitating the reaction mixture vigorously. Such vigorous agitation assures intimate contact among the reactants.

Subsequent to the reflux step, the additive mixture is recovered by well known techniques. For example, the product may be cooled, then filtered to remove the catalyst. If desired, further purification such as by distillation may be used to remove any remaining reactants, and undesirable byproducts. However, one of the key features of this invention is the formation of products which are useful without the need for extensive purification techniques.

While the above process contemplates conducting the reaction and reflux steps in a single reaction vessel, multiple reaction vessels may be used for each step. As indicated above, the reaction is conducted typically under superatmospheric pressures, whereas the reflux step may be conducted at superatmospheric pressure, atmospheric pressure, or subatmospheric pressure. Hence, it may be desirable to utilize separate vessels for the reaction and reflux steps, for example, a pressure vessel for the reaction step, and an atmospheric vessel for the post-treatment step may be used. The number and arrangement of vessels is not critical to the invention.

The additive mixture formed by the process of this invention may be used as is in oleaginous fluids as a lubricant additive or may be further admixed or reacted with an organophosphorus compound to form a mixed extreme pressure/antiwear agent. The formation of such mixed additives are described in U.S. Pat. Nos. 3,583,915, 3,520,426, 4,744,912, and 4,900,460; and Japan Kokai 59-10559 incorporated herein by reference as if fully set forth.

The following examples illustrate, but are not intended to limit, embodiments of the present invention.

EXAMPLE 1

Preparation of di-t-butyl polysulfide

A solid mixture of flowers of sulfur (8.56 grams, 0.268 gram-atoms) and alumina (2.0 grams, 0.20 mole) were placed in a 150 ml stainless steel autoclave. The autoclave was sealed and then flushed with nitrogen. After flushing, the autoclave was cooled down to 0° to −20° C. in a dry-ice/acetone cooling bath. Isobutylene (30 grams, 0.52 mol) and hydrogen sulfide (25 grams, 0.74 mol) were charged to the cool autoclave. The autoclave was then warmed to about 30° C. with a luke warm water bath, and then heated to 105°–110° C. in 10 minutes. The pressure increased within the autoclave to 6.9 mPa within the first 30 minutes, then gradually dropped to 4.5 mPa during the course of the reaction. During the reaction, the autoclave contents were stirred. After the 3 hour reaction time the autoclave was cooled to 10°–20° C. and the pressure was released from the reactor by venting the reactor through traps containing dilute NaOH, bleach and bromine in ethyl acetate. Once vented, the autoclave is again flushed with nitrogen. The resulting yellow oil was removed from the reator and analyzed utilizing gas chromatographic analysis. Analysis indicated 15 GC area % isobutylene, 29 GC area % tert-butyl mercaptan, 17 GC area % di-tert-butyl disulfide, 19 GC area % di-tertbutyl trisulfide and 16 GC area % di-tert-butyl tetrasulfide.

The resulting reaction mass from the above was transferred to a 100 mL round-bottomed flask which was equipped with an efficient condenser and having the above caustic and bleach scrubber attached to the vent line. The mixture was stirred vigorously for about 45 minutes in an oil bath maintained at 90°–100° C. Then the reaction mixture was cooled and filtered to remove the catalyst. The light-yellow product (36 grams) was obtained having the following constituents: 18 GC area % tertbutyl mercaptan, 23 GC area % di-tert-butyl disulfide, 50 GC area % di-tert-butyl trisulfide and 5.5 GC area % di-tert-butyl, tetrasulfide.

The following example illustrates the post-treatment step which selectively converts dialkyl higher-polysulfides to dialkyl trisulfides.

EXAMPLE 2

Post-treatment formation of trisulfides

Reaction masses prepared by the alumina-catalyzed sulfurization of isobutylene of Example 1 were transferred to a 100 mL round-bottomed flask equipped with an efficient condenser which was attached to NaOH and bleach traps. Each mixture was analyzed by gas chromatography without dilution. The mixtures were refluxed at atmospheric pressure by stirring the mixture at 90°–100° C. for about 45 minutes until evolution of gas ceased. After refluxing, the mixtures were cooled, filtered and analyzed again by gas chromatography. For each run, the analysis of the mixture before and after refluxing is indicated in the following Table 1. In the table, R represents tert-butyl and R' represents tert-butyl or an isomer or oligomer thereof and x>4.

TABLE I

| Run # | Post-treated | Composition (GC Area %) | | | | | | |
|---|---|---|---|---|---|---|---|---|
| | | $C_4H_8$ | RSH | R'SR' | $RS_2R$ | $RS_3R$ | $RS_4R$ | $R'S_xR'$ | $S_3/S_4$ |
| 1 | No | 9.3 | 32 | 2.6 | 22 | 18 | 13 | 1.3 | 1.4 |
|   | Yes | 0 | 16 | 2.8 | 31 | 43 | 5.2 | 0.8 | 8.2 |
| 2 | No | 4.5 | 31 | 1.9 | 22 | 21 | 17 | 2.0 | 1.2 |
|   | Yes | 0 | 15 | 2.0 | 24 | 51 | 7.2 | 0 | 7.1 |
| 3 | No | 7.9 | 32 | 1.8 | 19 | 19 | 16 | 1.8 | 1.2 |
|   | Yes | 0.6 | 11 | 2.1 | 31 | 44 | 8.7 | 1.6 | 5.1 |
| 4 | No | 6.1 | 31 | 1.8 | 21 | 17 | 20 | 1.9 | 0.9 |
|   | Yes | 0 | 15 | 1.9 | 24 | 50 | 7.4 | 0.7 | 6.8 |
| 5 | No | 13 | 30 | 1.9 | 20 | 14 | 16 | 2.1 | 0.9 |
|   | Yes | 0 | 14 | 2.1 | 25 | 50 | 7.2 | 1.1 | 6.9 |

The following example illustrates the use of alumina catalyst in multiple runs both in the sulfurization and posttreatment steps.

EXAMPLE 3

Isobutylene (30 grams), sulfur (8.56), hydrogen sulfide (25 grams), and alumina (2.0 grams) were reacted according to the general procedure of Example 1 above to give the product distributions indicated by Runs 1 and 2 of Table 2. Run 1A of Table 2 indicates the results of refluxing the product from generally in accordance with the procedure of Example 2 above. Subsequent to Run 1A, the liquid phase of the resulting mixture was removed leaving the used alumina in the flask. This used alumina was used in the post-treatment of the mixture in Run 2A which is the polysulfide mixture prepared in Run 2. In the table, the use of alumina catalyst from a previous polysulfide or post-treatment reaction is indicated for each run. Zero indicated indicates that fresh alumina catalyst was used. In the table, R represents tert-butyl.

TABLE 2

| Run # | Reactant(s) (Source) | Alumina (Source) | Composition (GC Area %) | | | | | |
|---|---|---|---|---|---|---|---|---|
| | | | $C_4H_8$ | RSH | $RS_2R$ | $RS_3R$ | $RS_4R$ | $S_3/S_4$ |
| 1 | $C_4H_8/S/H_2S$ | (0) | 10 | 32 | 25 | 20 | 13 | 1.5 |
| 1A | Post-treat. | Run 1 | 0 | 20 | 30 | 42 | 3.7 | 11 |
| 2 | $C_4H_8/S/H_2S$ | (0) | 15 | 29 | 18 | 19 | 16 | 1.2 |
| 2A | post-treat. | Run 1A | 0 | 18 | 23 | 50 | 5.6 | 8.9 |
| 3 | $C_4H_8/S/H_2S$ | Run 2 | 6.3 | 32 | 21 | 20 | 16 | 1.3 |
| 3A | Post-treat. | Run 2A | 0 | 17 | 24 | 49 | 5.7 | 8.6 |
| 4 | $C_4H_8/S/H_2S$ | Run 3 | 10 | 32 | 20 | 17 | 15 | 1.1 |
| 4A | Post-treat. | Run 3A | 0 | 19 | 24 | 49 | 5.0 | 9.7 |
| 5 | $C_4H_8/S/H_2S$ | Run 4 | 9.2 | 34 | 20 | 17 | 14 | 1.2 |
| 6 | $C_4H_8/S/H_2S$ | Run 5 | 8.2 | 26 | 23 | 18 | 19 | 1.0 |
| 6A | Post-treat. | Run 6 | 0 | 14 | 27 | 48 | 7.5 | 6.4 |

The following example illustrates the use of other catalysts in the formation of polysulfide mixtures.

EXAMPLE 4

A mixture of isobutylene (30 grams, 0.54 mol), sulfur (8.56 grams, 0.268 gram-atoms), hydrogen sulfide (26 grams, 0.76 mol), and the catalyst indicated in Table 3 were reacted under pressure for 3 hours generally in accordance with the procedure of Example 1. The resulting polysulfide mixture was analyzed by gas chromatographic analysis (GC) without any post-treatment. In the table R represents tert-butyl and R' represents tert-butyl or an isomer or oligomer thereof and X>4.

TABLE 3

| Run # | Catalyst | C$_4$H$_8$ | RSH | RS$_2$R | RS$_3$R | RS$_4$R | R'S$_x$R' | S$_3$/S$_4$ |
|---|---|---|---|---|---|---|---|---|
| 1 | None | 14 | 15 | 30 | 2.4 | 28 | 2.9 | 0.09 |
| 2 | MgO | 3.7 | 29 | 21 | 24 | 17 | 1.0 | 1.4 |
| 3 | Zeolite A | 8.5 | 39 | 24 | 4.7 | 18 | 2.0 | 0.26 |
| 4 | Primene-81R | 6.0 | 28 | 28 | 13 | 13 | 1.1 | 1.0 |

The following example illustrates the effect the reaction time has on the product composition.

EXAMPLE 5

Isobutylene (30 grams, 0.54 mol) was reacted with sulfur (8.56 grams, 0.268 gram-atoms) and hydrogen sulfide (26 grams, 0.76 mol) in the presence of alumina catalyst (2.0 grams, 0.020 mol) generally in accordance with the procedure of Example 1. The reaction was conducted for the periods of time indicated in the table. The resulting polysulfide mixture was analyzed by GC analysis without any post-treatment. In the table R represents tert-butyl and R' represents tert-butyl or an isomer or oligomer thereof and X>4.

TABLE 4

| Run # | Reaction time (HR) | C$_4$H$_8$ | RSH | RS$_2$R | RS$_3$R | RS$_4$R | R'S$_x$R' | S$_3$/S$_4$ |
|---|---|---|---|---|---|---|---|---|
| 1 | 1.0 | 15 | 1.7 | 9.2 | 16 | 49 | 8.0 | 0.33 |
| 2 | 2.0 | 20 | 22 | 13 | 16 | 22 | 3.2 | 0.73 |
| 3 | 3.0 | 13 | 31 | 19 | 17 | 14 | 1.2 | 1.2 |
| 4 | 3.0 | 15 | 29 | 17 | 19 | 16 | 1.2 | 1.2 |
| 5 | 4.0 | 9.0 | 34 | 20 | 17 | 14 | 1.2 | 1.2 |
| 6 | 5.0 | 5.0 | 32 | 25 | 20 | 13 | 1.5 | 1.5 |
| 7 | 5.0 | 5.0 | 35 | 24 | 21 | 13 | 1.6 | 1.6 |

The following example illustrates the catalytic activity of various forms of alumina catalyst in the formation of polysulfide mixtures.

EXAMPLE 6

Alumina catalyst from various commercial sources having different crystallinity forms, acidity and particle size were used as catalysts in the sulfurization of isobutylene. The reactions were carried out according to the general procedure of above. The properties of the catalyst as well as the GC analysis of the resulting product are indicated in Table 5. In the table R represents tert-butyl and R' represents tert-butyl or an isomer or oligomer thereof and X>4.

TABLE 5

| Run # | Alumina type | C$_4$H$_8$ | RSH | R'SR' | RS$_2$R | RS$_3$R | RS$_4$R | R'S$_x$R' | S$_3$/S$_4$ |
|---|---|---|---|---|---|---|---|---|---|
| 1 | Activated Basic 150 mesh | 12 | 27 | 1.5 | 18 | 14 | 21 | 2.7 | 0.7 |
| 2 | Activated Acidic 150 mesh | 6.1 | 31 | 1.6 | 21 | 17 | 20 | 1.9 | 0.9 |
| 3 | Gamma, 0.01μ 99.99% | 9.3 | 32 | 2.6 | 22 | 18 | 13 | 1.3 | 1.4 |
| 4 | Fused 325 mesh 10μ 99+% | 9.1 | 5.0 | 0 | 9.9 | 5.2 | 57 | 10 | 0.09 |
| 5 | Activated 99% 3.2 mm pellets | 13 | 30 | 2.0 | 20 | 14 | 16 | 2.1 | 0.9 |
| 6 | Alcoa CG-20 150 m$^2$/gram | 7.9 | 32 | 1.8 | 19 | 19 | 16 | 1.8 | 1.2 |
| 7 | Alcoa CP-100 150 m$^2$/gram | 4.5 | 31 | 1.9 | 22 | 21 | 17 | 2.0 | 1.2 |

Other embodiments of the invention are within the spirit and scope of the appended claims.

What is claimed is:

1. A method for preparing an essentially chlorine free additive mixture for oleaginous fluids containing less than 15 wt. % dialkyl higher-polysulfides, said process comprising:

a) forming a reaction mass comprising olefin, a sulfur source selected from hydrogen sulfide, flowers of sulfur, and a mixture of hydrogen sulfide and flowers of sulfur, and alumina catalyst;

b) agitating while heating the reaction mass to a temperature within the range of from about 50° to about 200° C. and for a period of time sufficient to form a reaction mixture of olefin, alkyl mercaptan, dialkyl disulfide, dialkyl trisulfide and dialkyl higher-polysulfide;

c) subsequently, cooling the reaction mixture to a temperature of less than about 35° C.;

d) removing a substantial portion of hydrogen sulfide and unreacted olefin from the reaction mixture; and e) refluxing the reaction mixture obtained in (d) for a period of time which is sufficient to convert at least a portion of the dialkyl higher-polysulfides to dialkyl trisulfide so as to obtain said additive mixture containing less than 15 wt. % dialkyl higher-polysulfides.

2. The method of claim 1 wherein the sulfur source is comprised of a mixture of hydrogen sulfide and flowers of sulfur.

3. The method of claim 1 wherein the olefin is isobutylene.

4. The method of claim 3 wherein the mole ratio of isobutylene to gram atoms of sulfur in the reaction mass is in the range of from about 1:0.5 to about 1:0.8.

5. The method of claim 1 wherein the catalyst is an activated alumina catalyst.

6. The method of claim 1 wherein the dialkyl higher-polysulfides is a mixture of dialkyl ($S_4$-$S_7$)polysulfides.

7. The method of claim 1 wherein the dialkyl trisulfide is a di-t-butyl trisulfide.

8. The method of claim 1 wherein the additive contains less than about 6 wt. % dialkyl higher-polysulfides.

9. The method of claim 8 wherein the sulfur source is comprised of a mixture of hydrogen sulfide and flowers of sulfur.

10. The method of claim 9 wherein the dialkyl trisulfide is a di-t-butyl trisulfide.

11. The method of claim 10 wherein the olefin is isobutylene.

12. The method of claim 11 wherein the mole ratio of isobutylene to gram atoms of sulfur in the reaction mass is in the range of from about 1:0.5 to about 1:0.8.

13. A process for preparing an essentially chlorine free mixture containing more than about 40 wt. % dialkyl trisulfide and having less than 15 wt. % dialkyl higher-polysulfides, said process comprising:

(a) reacting (i) olefin, (ii) hydrogen sulfide, (iii) flowers of sulfur, and (iv) a catalytic amount of an alumina catalyst to a reaction so as to form a reaction mass;

(b) agitating said reaction mass at a temperature within the range of from about 50° to 200° C. and for a period of time which are sufficient to form a reaction mixture containing olefin, alkyl mercaptan, and dialkyl polysulfides; and c) subsequently, cooling the reaction mixture to a temperature of less than about 35° C.;

d) removing a substantial portion of hydrogen sulfide and unreacted olefin from the reaction mixture; and e) refluxing said reaction mixture obtained in (d) for a period of time and at a temperature sufficient to form said chlorine free mixture comprising more than about 40 wt. % dialkyl trisulfide, and less than 15 wt. % dialkyl higher-polysulfides.

14. The method of claim 13 wherein the olefin is isobutylene.

15. The method of claim 14 wherein the mole ratio of isobutylene to gram atoms of sulfur in (a) is in the range of from about 1:0.5 to about 1:0.8.

16. The method of claim 15 wherein the catalyst is an activated alumina catalyst.

17. The method of claim 16 wherein the dialkyl higher-polysulfides is a mixture of dialkyl ($S_4$-$S_7$)polysulfides.

18. The method of claim 17 wherein the dialkyl trisulfide is a di-t-butyl trisulfide.

19. The method of claim 18 wherein the mixture contains less than about 6 wt. % dialkyl higher-polysulfides.

* * * * *